United States Patent
Lange et al.

(10) Patent No.: US 6,455,725 B1
(45) Date of Patent: Sep. 24, 2002

(54) SUBSTITUTED CINNAMIC ACIDS AND CINNAMIC ACID ESTERS

(75) Inventors: Walter Lange, Odenthal; Joachim Komoschinski, Köln; Guido Steffan, Odenthal; Ernst Kysela, Bergisch Gladbach, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/762,838

(22) PCT Filed: Aug. 9, 1999

(86) PCT No.: PCT/EP99/05735

§ 371 (c)(1),
(2), (4) Date: Feb. 13, 2001

(87) PCT Pub. No.: WO00/10963

PCT Pub. Date: Mar. 2, 2000

(30) Foreign Application Priority Data

Aug. 17, 1998 (DE) .......................................... 198 37 069

(51) Int. Cl.⁷ ............................................ C07C 261/00
(52) U.S. Cl. ........................... 560/28; 560/55; 562/104; 562/105; 562/493
(58) Field of Search ..................... 560/28, 55; 562/493, 562/105, 104

(56) References Cited

U.S. PATENT DOCUMENTS

| | | | |
|---|---|---|---|
| 5,231,223 A | | 7/1993 | Bader .......................... 562/87 |
| 5,300,675 A | * | 4/1994 | Elango et al. |
| H1705 H | * | 1/1998 | Dumas et al. |
| 5,708,033 A | * | 1/1998 | Kelley et al. |
| 5,869,657 A | * | 2/1999 | Annis et al. |
| 5,968,985 A | | 10/1999 | Kuno et al. .................. 514/617 |
| 6,018,071 A | | 1/2000 | Annis et al. .................. 560/80 |
| 6,080,856 A | | 6/2000 | Annis et al. .................. 544/66 |
| 6,117,881 A | | 9/2000 | Bombrun .................... 514/292 |

OTHER PUBLICATIONS

Petrova et al, Chemical Abstracts, vol. 79, 1973, nop. 91891m; Petrova et al, Chemical Abstracts, vol. 97, 1982, No. 109843f, Petrova et al, Chemical Abstracts, vol. 82, 1975, No. 31200n.*
Sengupta et al, Journal of Chemical Society Perkin Transactions, 1, 1993.*
Aldrich, Handbook of Fine Chemicals, 1996–97, pp. 66, 75 and 78.*
Petrova et al, Chemical Abstracts, vol. 82, 1975 No. 31200n.*
Petrova et al, Chemical Abstracs, vol. 79, 1973 No. 91891m.*
Petrova et al, Chemical Abstracts, vol. 97, 1982, No. 109843f.*
J. Pharm. Sci. 67(1), (month unavailable) 1978, pp. 80–83, E.S. Stratford, L. M. Smith, and G.W. Tomecko, Potential Hypocholesteremic Derivatives of Styrylacetic Acid II: cis– and trans–3–Methyl–4–phenyl–3–butenoic Acid Analogs.
Chemical Abstracts, 97, 1982, No. 109843f.
Chemical Abstracts 82, 1972, No. 31200n.
Chemical Abstracts, 79, 1973, No. 91891m.

* cited by examiner

*Primary Examiner*—Alan L. Rotman
*Assistant Examiner*—Hèctor M. Reyes
(74) *Attorney, Agent, or Firm*—Joseph C. Gil; Diderico van Eyl

(57) ABSTRACT

The invention relates to substituted cinnamic acids and cinnamic acid esters of formula (I), wherein X represents F, Cl or J and $R^1$ and $R^2$ are the same or different and represent hydrogen, an optionally substituted $C_1$–$C_{10}$-alkyl radical or an optionally substituted benzyl radical. Substituted indanone carboxylic acid esters are produced using said substituted cinnamic acid and cinnamic acid ester in a technically simple and non-dangerous manner as far as safety is concerned.

8 Claims, No Drawings

SUBSTITUTED CINNAMIC ACIDS AND CINNAMIC ACID ESTERS

BACKGROUND OF THE INVENTION

The present invention relates to substituted cinnamic acids and cinnamic acid esters, to a process for their preparation and to their use for synthesizing insecticide precursors.

The synthesis of insecticides is of high importance. Important intermediates in this synthesis are the substituted indanonecarboxylic acid esters and their salts.

WO 95/29171, for example, discloses a process for preparing oxadiazines which are used in the field of crop protection for controlling arthropods. In the multistep preparation process, use is made, inter alia, of substituted indanonecarboxylic acid ester intermediates. The synthesis of the substituted indanonecarboxylic acid esters comprises a Friedel-Crafts reaction of para-substituted phenylacetyl halides with ethylene in the presence of a Lewis acid and an inert solvent with formation of a 2-tetralone of the formula A, where $R^1$ represents F, Cl or $C_1$–$C_3$-fluoroalkoxy,

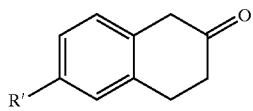
A the reaction of the compound A with peroxycarboxylic acids with formation of substituted arylpropionic acids of the formula B,

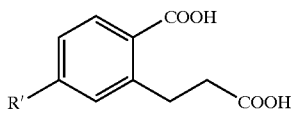
B the esterification of the substituted arylpropionic acids of the formula B with $C_1$–$C_3$-alcohols in the presence of an acid catalyst with formation of the substituted arylpropionic acid esters of the formula C, where R" represents $C_1$–$C_3$-alkyl,

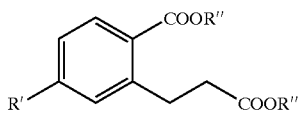
C and the reaction of the compounds C with a base with ring closure and formation of the substituted indanonecarboxylic acid ester of the formula D

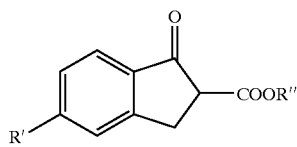
D

This synthesis of the substituted indanonecarboxylic acid esters has the disadvantage that the addition of from 0.9 to 1.5 molar equivalents of a Lewis acid, such as, for example, aluminum trichloride, is required in the Friedel-Craft reaction for the reaction of the phenylacetyl halides with ethylene. As a consequence, large amounts of salts are produced during work-up of the reaction mixture, and thus corresponding volumes of contaminated waste water. Additionally, this synthesis requires the use of peroxycarboxylic acids, such as, for example, peroxyacetic acid, for cleaving the 2-tetralone. For this purpose, the peroxycarboxylic acids have to be employed in an amount of from 2.5 to 3.5 molar equivalents. If the reaction is carried out on an industrial scale, this causes safety risks. Therefore, the reaction temperature has to be exactly maintained and, furthermore, the addition of the peroxycarboxylic acid has to be controlled accurately to avoid an accumulation of excessive amounts of excess peroxycarboxylic acid in the reaction system.

It is furthermore known from J. Pharm. Sci. 67(1) 1978, 81, to prepare the chloro-substituted indanonecarboxylic acid ester 5-chloro-2-methoxycarbonyl-1-indanone starting from 3-chlorobenzaldehyde. Here, 3-chlorobenzaldehyde is initially reacted in pyridine with malonic acid to give 3-chlorocinnamic acid. Following hydrogenation of the ethylenic double bond and cyclization to the 5-chloro-1-indanone, the latter is then reacted with dimethyl carbonate in the presence of sodium hydride and benzene as solvent to give 5-chloro-2-methoxycarbonyl-1-indanone. This synthesis method has the disadvantage of the multistep mechanism which considerably increases the likelihood of the formation of various by-products, which is reflected in only a low yield of 48%. Additionally, the total reaction requires the repeated use of substances such as sodium hydride and benzene, which are expensive, problematic with respect to safety or hazardous to health.

Chemical Abstracts 97, 1982, 109843f discloses 5-bromo-2-carboxy-cinnamic acid which is obtained by oxidative cleavage of 6-bromo-2-naphthol and is then cyclized, reacted with $PCl_5$ and $NH_3$ to give the amide and subsequently, with ring enlargement, reacted in the presence of NaOCI to give 6-bromo-isoquinolin-1-one.

Also known from Chemical Abstracts 82, 1975, 31200n and 79, 1973, 91891m, is the oxidative cleavage of 6-bromo-2-naphthol with formation of 5-bromo-2-carboxy-cinnamic acid, which leads, via a plurality of steps of amidation, Hoffmann rearrangement and cyclization, to the corresponding substituted indoles.

WO 97/43287 A1 discloses, in a general manner, substituted cinnamic acids and cinnamic acid chlorides which may be substituted on the phenyl ring by a radical $R^1$ and one or two further radicals $R^2$, a large number of meanings being possible for these radicals. Also described is the reaction of the substituted cinnamic acids and cinnamic acid chlorides with other complex starting materials to give specific carboline derivatives which are used as cGMP-PDE inhibitors for cardiovascular indications.

WO 96/04241 A1 discloses, in the form of preparation 45, a cinnamic acid which is substituted in one m-position of the 2-carboxyvinyl radical by methyl carboxylate and in the other m-position by iodine. WO 96/04241 is focused on the preparation of specific, pharmaceutically active benzoylguanidine derivatives, in which the preparation 45 is also used.

EP-A-0 508 264 discloses a process for preparing broadly defined arylolefins which, in a general manner, also include substituted cinnamic acids and cinnamic acid esters. The arylolefins that can be prepared are used in very different areas, for example as optical brighteners, as precursors for optical brighteners, as intermediates for pharmaceutics or as UV absorbers.

DESCRIPTION OF THE INVENTION

Accordingly, it was the object of the present invention to provide intermediates which can be used to synthesize substituted indanonecarboxylic acid esters in a technically simple manner, which does not involve any safety risks.

This object is achieved by substituted cinnamic acids and cinnamic acid esters of the formula (I)

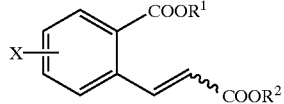

(I)

where X represents F, Cl or J and $R^1$ and $R^2$ are identical or different and represent hydrogen, an optionally substituted $C_1$–$C_{10}$-alkyl radical or an optionally substituted benzyl radical.

These substituted cinnamic acids or cinnamic acid esters are distinguished by the fact that, for the first time, they allow, in an unexpectedly simple two-step process, a low-cost synthesis of substituted indanonecarboxylic acid esters.

In the substituted cinnamic acids or cinnamic acid esters, X represents F, Cl J, preferably chlorine.

$R^1$ and $R^2$ are identical or different and represent hydrogen, an optionally substituted $C_1$–$C_{10}$-alkyl radical or an optionally substituted benzyl radical. Preferably, $R^1$ and $R^2$ independently of one another represent hydrogen, methyl, ethyl, propyl, i-propyl, n-butyl, i-butyl, tert butyl, n-pentyl, i-pentyl, n-hexyl, i-hexyl, n-heptyl, i-heptyl, n-octyl, i-octyl, n-nonyl, i-nonyl, n-decyl or i-decyl. In particular, $R^1$ and $R^2$ independently of one another represent hydrogen or methyl.

If the $C_1$–$C_{10}$-alkyl radical is substituted as radical $R^1$ or $R^2$, these substituents can be halogen, hydroxyl or $C_6$–$C_{12}$-aryl radicals. The benzyl radical as radical $R^1$ or $R^2$ can be substituted by halogen, hydroxyl, $C_1$–$C_{10}$-alkyl or $C_6$–$C_{12}$-aryl radicals.

In the cinnamic acids or cinnamic acid esters of the formula (I), the substituent X is preferably in the 5-position to the acrylic acid or acrylic acid ester radical.

Preferred compounds of the formula (I) are methyl 4-chloro-2-(3-methoxy-3-oxo-1-propenyl)benzoate, 4-chloro-2-(3-methoxy-3-oxo-1 -propenyl)-benzoic acid, 4-fluoro-2-(3-methoxy-3-oxo-1-propenyl)benzoic acid, methyl 4-chloro-2-(3-hydroxy-3-oxo-1-propenyl)benzoate or 4-chloro-2-(3-hydroxy-3-oxo-1-propenyl)benzoic acid.

The substituted cinnamic acids or cinnamic acid esters of the formula (I) can be prepared by a variation of the Heck reaction (Process A).

The invention provides a process for preparing the substituted cinnamic acids and cinnamic acid esters of the formula (I) by reacting diazonium salts of the formula (II0 with acrylic acid derivatives of the formula (III) in the presence of a palladium-containing catalyst, where X, $R^1$ and $R^2$ are as defined in formula (I) and A- represents halide, preferably chloride or bromide, sulfate, hydrogen sulfate, nitrate, phosphate, acetate or tetrafluoroborate, characterized in that the reaction is carried out in the absence of bases. This synthesis route is particularly advantageous and thus preferred.

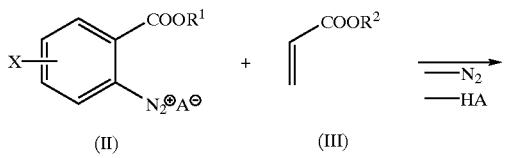

-continued

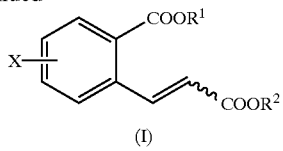

(I)

X, $R^1$ and $R^2$ preferably have the meanings which have also been mentioned as being preferred for the formula (I). A- preferably represents chloride, sulfate, hydrogen sulfate, acetate or tetrafluoroborate.

The reaction principle of this process A is generally known as Matsuda variant of the Heck reaction. According to EP-A-0 584 043, for example, compounds of the formula Ar—$CHR_a$—$CHR_bR_c$ can be prepared in a very general manner, $R_a$, $R_b$ and $R_c$ independently of one another representing hydrogen or a substituent which is inert to hydrogenation and Ar representing an optionally substituted $C_6$–$C_{20}$-aryl- or $C_3$–$C_{20}$-heteroaryl radical. To this end, in a first step, 1 molar equivalent of the diazonium cation Ar—$N_2^+$ is reacted with at least 1 molar equivalent of a compound $CR_a$=$CR_bRC$ with formation of the compound Ar—$CHR_a$=$CHR_bR_c$, the reaction being carried out in the presence of a catalytic amount of a homogeneous palladium catalyst. Furthermore, addition of a base is a necessary requirement. In particular when the Heck reaction is carried out on an industrial scale, the addition of from 1 to 10 molar equivalents of this base involves additional costs and a complicated work-up of the reaction mixture. In a second step, the compound Ar—$CHR_a$=$CHR_bR_c$ is hydrogenated to give the compound Ar—$CHR_a$—$CHR_bR_c$. This hydrogenation step is characterized in that the reaction is carried out in the presence of catalytic amounts of a heterogeneous palladium catalyst, which is obtained from the homogeneous palladium catalyst of the first step by reduction prior to the second step.

EP-A-0 584 043 discloses explicitly and especially only those compounds Ar—$HR_a$=$CHR_bR_c$ and Ar—$CHR_a$—$CHR_bR_c$ which carry a sulfonic acid group and optionally other substituents on the aryl radical Ar. However, EP-A-0 584 043 does not disclose the cinnamic acids or cinnamic acid esters of the formula (I) according to the invention which are substituted on the radical Ar=phenyl by a halogen radical and a carboxylic acid or carboxylic acid ester radical, nor their specific preparation according to process A, nor their excellent suitability for use as starting materials for the preparation of substituted indanonecarboxylic acid esters. Compared to the process of EP-A-0 584 043, process A is distinguished by the fact that it is possible to obtain excellent high yields even without the addition of a base, which enhances the economic attraction of the process with respect to work-up and generation of waste water. It is even possible to carry out the process in a solution of mineral or sulfuric acid.

F EP-A-0 508 264, too, discloses the principle of process A, i.e. the preparation, from aryldiazonium salts and olefins in the presence of a palladium catalyst, of the corresponding aryl olefins. However, as in the case of EP-A-0 584 043, the emphasis of EP-A-0 508 264 is placed on compounds which carry a sulfonic acid group on the aryl radical. The selected cinnamic acids or cinnamic acid esters according to the invention and their suitability for preparing substituted indanonecarboxylic acid esters are not explicitly disclosed. According to EP-A-0 508 264, too, in the Heck reaction bases are added and also, favorably, ligands, such as tri-arylphosphines or bis(diarylphosphine)alkanes capable of forming complexes with the palladium or the palladium salts. In contrast, process A is characterized by the fact that the addition of such auxiliary ligands to the catalyst is usually not required.

The Heck reaction according to variant A is carried out using palladium(II)salts, such as $PdCl_2$, $PdBr_2$, $Pd(NO_3)_2$, $H_2PdCl_4$, $Pd(CH_3COO)_2$, $[PdCl_4]Na_2$, $[PdCl_4]Li_2$, $[PdCl_4]K_2$, or palladium(I) acetylacetonate. $PdCl_2$, $Pd(CH_3COO)_2$ and palladium(II) acetylacetonate are particularly preferred. Usually, 0.001–10 mol % of the palladium-containing catalyst, based on the diazonium salt of the formula (II), are employed.

The reaction temperature for variant A should be below the decomposition temperature of the diazonium ion; in general, variant A is carried out at from −20° C. to 100° C., preferably from 20 to 80° C. and in particular from 40 to 65° C. The reaction can be carried out with addition of suitable solvents; usually, water, alcohols, preferably methanol, ethanol, propanol, i-propanol or butanol, formic acid, tetrahydrofuran or acetonitrile are added.

The diazonium salts of the formula (II) used in process A are obtainable by reacting halogenated anthranilic acid derivatives with sodium nitrite in acidic aqueous solution or with methyl nitrite in acidic methanol. If sodium nitrite is used, preferably in aqueous solution acidified with sulfuric acid, small amounts of isopropanol may also additionally be present. If methyl nitrite in methanol acidified with sulfuric acid is used, the reaction is generally carried out anhydrous to avoid unnecessary hydrolysis of methyl nitrite. It is advantageous that no organic solvents such as dimethylformamide (DMF), N-methylpyrrolidone (NMP) or dimethyl sulfoxide (DMSO) have to be used in this diazotization. Also advantageous are the low reaction temperatures. The cinnamic acids or cinnamic acid esters of the formula (I) usually precipitate from an aqueous reaction mixture or can be precipitated by additional addition of water. The resulting solids can be dissolved for subsequent reactions by adding organic solvents.

Instead of the diazonium salts of the formula (II), it is also possible to react in the Heck coupling halogenated aromatic compounds of the formula (IV) with the acrylic acid derivatives of the formula (III) (Process B), X, $R^1$ and $R^2$ being as defined for formula (I). Y represents bromine or iodine. EP-A-0 688 757, too, discloses the reaction of such halogenated aromatic compounds with olefins, the palladium catalysts used being specific palladacycles, in particular μ-bridged dipalladium complexes.

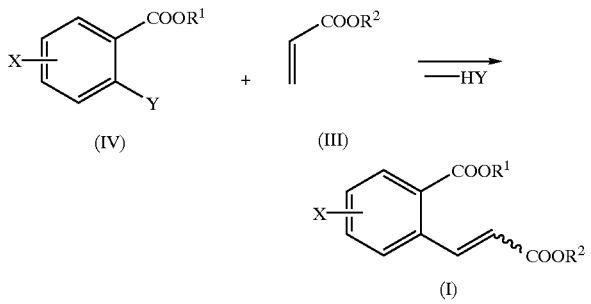

The present invention furthermore provides the use of substituted cinnamic acids and cinnamic acid esters of the formula (I) for preparing substituted indanonecarboxylic acid esters of the formula (VII)

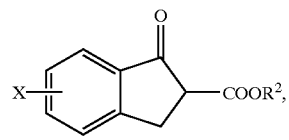

where
X and $R^2$ are as defined for formula (I).

A preferred embodiment of this use is characterized in that the substituted cinnamic acids and cinnamic acid esters of the formula (I) are, in a first step, hydrogenated with hydrogen in the presence of a hydrogenation catalyst, with formation of substituted arylpropionic acids of the formula (VIII),

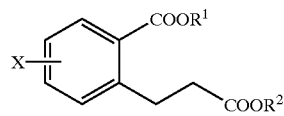

which are then, in a second step, cyclized in the presence of a base, with formation of the substituted indanonecarboxylic acid esters of the formula (VIH), where X, $R^1$ and $R^2$ in the formulae (VII) and (VIII) each have the meanings mentioned for the formula (I).

The cinnamic acids or cinnamic acid esters of the formula (I) according to the invention obtained by process A or B can be introduced with or without prior isolation from the respective reaction mixtures into the first step for the synthesis of the substituted indanonecarboxylic acid esters. If, following their preparation by process A or B, the cinnamic acids or cinnamic acid esters of the formula (I) are not isolated, but the entire reaction mixture is used for preparing the indanonecarboxylic acid esters of the formula (VII), the palladium catalyst of the Heck reaction acts as hydrogenation catalyst for the preparation of the arylpropionic acids of the formula (VIII). If the cinnamic acids or cinnamic acid esters are isolated as solids from the reaction mixture of process A or B, a hydrogenation catalyst may be added for the hydrogenation to the arylpropionic acids. However, this is not necessary in all cases if the isolated solid still contains small amounts of the catalyst used in the Heck reaction. If a hydrogenation catalyst is additionally added, it is usually a palladium or platinum catalyst supported on activated carbon.

The hydrogenation to the saturated arylpropionic acids of the formula (VIII) is carried out in the presence of hydrogen and, usually, water, mineral acids and/or alcohols as solvent.

The mineral acid present is usually sulfuric acid, unless the cinnamic acids or cinnamic acid esters are isolated from the reaction mixture of the preceding processes prior to their hydrogenation. The alcohols present can be, for example, methanol, ethanol, propanol, i-propanol or xylol.

The hydrogenation is usually carried out under a pressure of 1–100 bar.

The cyclization of the substituted arylpropionic acids of the formula (VIII) to the corresponding substituted indanonecarboxylic acid esters of the formula (VII) is carried out in the presence of a strong base and a suitable solvent. Usually, the strong base used is an alkali metal hydride, preferably sodium hydride, or an alkali metal alkoxide, preferably sodium alkoxide. Suitable solvents were found to be toluene, xylene, benzene or the alcohols which correspond to the alkali metal alkoxides. In particular, xylene or methanol is used. At a reaction temperature of from 60 to 90° C. and a reaction pressure of from 100 to 500 kPa, the reaction time is from 0.5 to 10 hours. Here, the indanonecarboxylic acid esters are obtained as alkali metal salt and are additionally neutralized by addition of an acid, such as, for example, glacial acetic acid or dilute aqueous mineral acid, and then isolated by filtration or extraction. For the reaction conditions of the cyclization of the substituted arylpropionic acids of the formula (VIJI), reference is otherwise made to the corresponding disclosure of WO 95/29 171, which is expressly incorporated herein by way of reference.

The invention is further described in the following illustrative examples in which all parts and percentages are by weight unless otherwise indicated.

EXAMPLE 1

Methyl 4-Chloro-2-(3-methoxy-3-oxo-1-propenyl)-benzoate

Methyl nitrite is generated from 76 g of sodium nitrite in 55 ml of methanol and 183 ml of water using 80 ml of 50% strength sulfuric acid, and the methyl nitrite is introduced at from 10 to 15° C. into a mixture of 171.5 g of 2-amino-4-chlorobenzoic acid, 800 ml of methanol and 200 ml of concentrated sulfuric acid. The mixture is stirred for one hour, and 8 g of amidosulfonic acid are then added and excess methyl nitrite is removed from the reaction mixture by passing a stream of nitrogen over the mixture. 86 g of methyl acrylate and 666 mg of palladium acetylacetonate are then added, and the mixture is heated at 40° C. for 3 hours. 1600 ml of methanol are then added, and the mixture is heated at the boil for a further 3 hours. Following addition a of 2500 ml of ice-water, the resulting precipitate is filtered off, washed with water and then dried. This gives 207 g of methyl 4-chloro-2-(3-methoxy-3-oxo-1-propenyl)-benzoate of melting point 87–89° C.

EXAMPLE 2

4-Fluoro-2-(3-methoxy-3-oxo-1-propenyl)-benzoic Acid

At 0C, a solution of 0.52 g of sodium nitrite in 1 ml of water is added within a period of 30 minutes to a mixture of 1 g of 2-amino-4-fluorobenzoic acid, 15 ml of water and 6.24 ml of concentrated sulfuric acid. The mixture is then stirred for one hour. Following addition of 0.3 g of amidosulfonic acid, 0.7 g of methyl acrylate in 9 ml of isopropanol are added dropwise, and 10 mg of palladium acetylacetonate are added. After 4 hours at 40° C., 30 ml of water are added and the resulting precipitate is filtered off. Drying gives 1.1 g of 4-fluoro-2-(3-methoxy-3-oxo-1-propenyl)-benzoic acid of melting point 151–153° C.

EXAMPLE 3

Methyl 4-Chloro-2-(3-methoxy-3-oxo-1-propenyl)-benzoate

At 2° C., a solution of 79.5 g of sodium nitrite in 150 ml of water is added to a mixture of 185.5 g of methyl 2-amino-4-chlorobenzoate, 785 ml of water and 190.5 ml of concentrated sulfuric acid. Subsequently, the mixture is stirred for 30 minutes, and 5.3 g of amidosulfonic acid are then added. The resulting reaction mixture is added dropwise to 108.2 g of methyl acrylate. 766 mg of palladium acetylacetonate are then added to the reaction mixture, which is then heated to 40° C. After a further 3.5 hours at 40° C., the resulting precipitate is filtered off, giving, after drying, 248.3 g of methyl 4-chloro-2-(3-methoxy-3-oxo-1-propenyl)-benzoate of melting point 87–89° C.

EXAMPLE 4

Methyl 4-Chloro-2-(3-hydroxy-3-oxo-1-propenyl)-benzoate

At 2° C., a solution of 5.96 g of sodium nitrite in 11.3 ml of water is added to a mixture of 14 g of methyl 2-amino-4-chlorobenzoate, 59 ml of water and 14.3 ml of concentrated sulfuric acid. The reaction mixture is subsequently stirred for 20 minutes and then added a little at a time to 6.9 g of acrylic acid, 57 mg of palladium acetylacetonate being added after the first portion. After 4 hours at 40° C., the precipitated solid is filtered off, giving, after washing and drying, 18.5 g of methyl 4-chloro-2-(3-hydroxy-3-oxo-1-propenyl)-benzoate.

EXAMPLE 5

4–Chloro-2-(3-hydroxy-3-oxo-1-propenyl)-benzoic Acid

At 2° C., a solution of 2.98 g of sodium nitrite in 5.65 ml of water is added to a mixture of 6.43 g of 2-amino-4-chlorobenzoic acid, 29.5 ml of water and 14.3 ml of concentrated sulfuric acid. 0.4 g of amidosulfonic acid are subsequently added, and this reaction mixture is then added dropwise to 2.7 g of acrylic acid and 28.5 mg of palladium acetylacetonate. After 4 hours at 40° C., the precipitated solid is filtered off, giving 7.48 g of 4-chloro-2-(3-hydroxy-3-oxo-1-propenyl)-benzoic acid of melting point 200–202° C.

Analogously, 6.7 g of product are obtained using 21 mg of palladium acetate instead of 28.5 mg of palladium acetylacetonate.

EXAMPLE 6

Methyl 4-Chloro-2-(3-methoxy-3-oxo-1-propanyl)-benzoate 5 g of methyl 4-chloro-2-(3-hydroxy-3-oxo-1-propenyl)-benzoate in the form of the isolated solid from Example 4 in 75 ml of methanol are hydrogenated without addition of hydrogenation catalyst, at from 20 to 30° C. and a hydrogen pressure of 20 bar. Filtration through Celite® and removal of the solvents under reduced pressure gives 3.3 g of product which, according to gas chromatography, contains 88% of methyl 4-chloro-2-(3-methoxy-3-oxo-1-propenyl)-benzoate.

The same product is obtained using, instead of methyl 4-chloro-2-(3-hydroxy-3-oxo-1-propenyl)-benzoate, methyl 4-chloro-2-(3-methoxy-3-oxo-1 -propenyl)-benzoate from Example 1.

EXAMPLE 7

4–Chloro-2-(3-methoxy-3-oxo-1-propanyl)-benzoic Acid

Without addition of an additional hydrogenation catalyst, 43 g of 4-chloro-2-(3-hydroxy-3-oxo-1-propenyl)-benzoic acid in the form of the isolated solid from Example 5 in 400 ml of methanol are hydrogenated at 40° C. and a hydrogen pressure of from 20 to 40 bar. Filtration through Celite® and removal of the solvents under reduced pressure gives 35.3 g of product which, according to gas chromatography, contains 81% of 4-chloro-2-(3-methoxy-3-oxo-1-propenyl)-benzoic acid. The same product is obtained using, instead of 4-chloro-2-(3-hydroxy-3-oxo-1-propenyl)-benzoic acid, 4-chloro-2-(3-methoxy-3-oxo-1-propenyl)-benzoic acid.

EXAMPLE 8

Methyl 4-Chloro-2-(3-methoxy-3-oxo-1-propanyl)-benzoate 26.1 g of the methyl 4-chloro-2-(3-methoxy-3-oxo-1-propenyl)-benzoate prepared according to Example 1 are taken up in 300 ml of methanol and transferred into an autoclave and then hydrogenated at 30° C. and a hydrogen pressure of 30 bar for 5 h, until the theoretical amount of hydrogen has been taken up. The substance contains the palladium catalyst required for the Heck coupling, so that separate addition of a hydrogenation catalyst can be dispensed with. The pressure is reduced to 1 bar, and insoluble components are then filtered off. Solvent is then removed under reduced pressure until the hydrogenation product precipitates. Recrystallization gives 21 g of methyl 4-chloro-2-(3-methoxy-3-oxo-1-propanyl)-benzoate.

EXAMPLE 9

Methyl 4-Chloro-2-(3-methoxy-3-oxo-1-propanyl)-benzoate 26.1 g of the methyl 4-chloro-2-(3-methoxy-3-oxo-1-propenyl)-benzoate obtained according to Example 3 are taken up in 250 ml of methanol, about 1 g of activated carbon is added, the mixture is stirred under reflux and the hot mixture is filtered, this step removing the residual amounts of palladium catalyst from the Heck reaction. The filtrate, cooled again to room temperature, is then admixed with 1.5 g of a 5% strength platinum/carbon catalyst and hydrogenated at 30° C. and a hydrogen pressure of 5 bar for about 4 to 5 h, until the theoretical amount of hydrogen has been taken up. The pressure is reduced, the catalyst is filtered off and the solvent is removed from the mixture, thus giving 25.2 g of 4-chloro-2-(3-methoxy-3-oxo-1-propanyl)-benzoic acid ester.

EXAMPLE 10

2–Carboxymethyl-5-chloroindan-1-one 108 g of methyl 4-chloro-2-(3-methoxy-3-oxo-1-propenyl)-benzoate are dissolved in 300 ml of methanol, and 80 g of sodium methoxide are then added. The mixture is then heated at 70° C. and some of the methanol is distilled off, such that the reaction mixture can still be stirred. After 2 h, 400 ml of toluene are added slowly, and the remaining methanol is removed. The mixture is then stirred for another 0.5 h and then cooled to room temperature. 10 g of acetic acid are then added dropwise to the mixture, which is then diluted with 500 ml of water and adjusted to pH 4–5 using 1 N hydrochloric acid. The toluene phase is concentrated until the product precipitates. Following filtration, the product can be recrystallized from hexane. This gives 93.5 g of 2-carboxymethyl-5-chloroindan-1-one.

Although the present invention has been described in detail with reference to certain preferred versions thereof, other variations are possible. Therefore, the spirit and scope of the appended claims should not be limited to the description of the versions contained therein.

What is claimed is:

1. A substituted cinnamic acid or cinnamic acid ester of the formula (I)

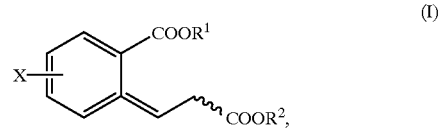

(I)

wherein X represents F, Cl or I and $R^1$ and $R^2$ are identical or different and represent hydrogen, an optionally substituted $C_1$–$C_{10}$-alkyl radical or an optionally substituted benzyl radical.

2. The substituted cinnamic acid or cinnamic acid ester as claimed in claim 1, wherein X represents chlorine and independently thereof $R^1$ and $R^2$ are identical or different and represent hydrogen, methyl, ethyl, propyl, i-propyl, n-butyl, i-butyl, tert butyl, n-pentyl, i-pentyl, n-hexyl, i-hexyl, n-heptyl, i-heptyl, n-octyl, i-octyl, n-nonyl, i-nonyl, n-decyl or i-decyl.

3. The substituted cinnamic acid or cinnamic acid ester as claimed in claim 1, wherein the $C_1$–$C_{10}$-alkyl radical as radical $R^1$ or $R^2$ is substituted by halogen, hydroxyl or $C_6$–$C_{12}$-aryl radicals and independently thereof the benzyl radical as radical $R^1$ or $R^2$ is substituted by halogen, hydroxyl, $C_1$–$C_{10}$-alkyl- or $C_6$–$C_{12}$aryl radicals.

4. The substituted cinnamic acid or cinnamic acid ester as claimed in claim 1, wherein the cinnamic acid or cinnamic acid ester is methyl 4-chloro-2-(3-methoxy-3-oxo-1-propenyl)benzoate, 4-chloro-2-(3-methoxy-3-oxo-1-propenyl)-benzoic acid, 4-fluoro-2-(3-methoxy-3-oxo-1-propenyl)benzoic acid, methyl 4-chloro-2-(3-hydroxy-3-oxo-1-propenyl)benzoate or 4-chloro-2-(3-hydroxy-3-oxo-1-propenyl)benzoic acid.

5. A process for preparing a substituted cinnamic acid or a cinnamic acid ester of the formula (I)

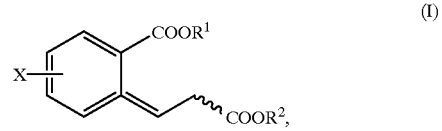

(I)

wherein X represents F, Cl or I and $R^1$ and $R^2$ are identical or different and represent hydrogen, an optionally substituted $C_1$–$C_{10}$-alkyl radical or an optionally substituted benzyl radical;

comprising reacting diazonium salts of the formula (II)

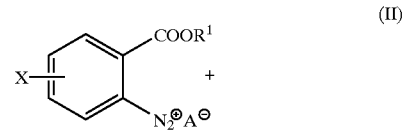

(II)

with acrylic acid derivatives of the formula (III)

(III)

in the presence of a palladium-containing catalyst, wherein X, $R^1$ and $R^2$ are as defined in formula (I) and $A^\ominus$ represents a halide, a sulfate, hydrogen sulfate, a nitrate, a phosphate, an acetate or tetrafluoro-borate, and wherein the reaction is carried out in the absence of bases.

6. The process of claim 5, wherein the palladium-containing catalyst used is a palladium(II) salt.

7. The process according to claim 5, wherein from about 0.001 to about 10 mol % of the palladium-containing catalyst, based on the diazonium salt of the formula (II), are used and, independently thereof, the process is carried out at a temperature that ranges from about −20 to about 100° C.

8. A process for preparing a substituted indanonecarboxylic acid ester of the formula (VII)

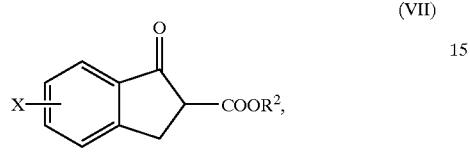
(VII)

wherein X represents F, Cl or I and $R^1$ and $R^2$ are identical or different and represent hydrogen, an optionally substituted $C_1$–$C_{10}$-alkyl radical or an optionally substituted benzylradical, comprising (A) hydrogenating, in the presence of a hydrogenation catalyst, a substituted cinnamic acid or cinnamic acid ester of the formula (I)

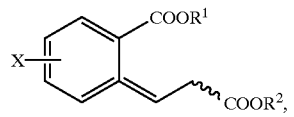
(I)

wherein X represents F, Cl or I and $R^1$ and $R^2$ are identical or different and represent hydrogen, an optionally substituted $C_1$–$C_{10}$-alkyl radical or an optionally substituted benzyl radical;

and forming a substituted arylpropionic acid of the formula (VIII),

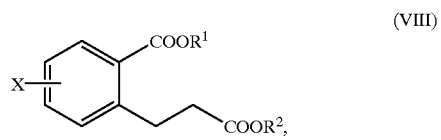
(VIII)

and (B) cyclizing the substituted arylpropionic of formula (VIII) in the presence of a base.

* * * * *